United States Patent [19]

Mattson et al.

[11] Patent Number: 5,703,239

[45] Date of Patent: Dec. 30, 1997

[54] INDANYLPIPERIDINES AS MELATONERGIC AGENTS

[75] Inventors: Ronald J. Mattson, Meriden; John D. Catt, Southington, both of Conn.

[73] Assignee: Bristol-Myers Squibb Company, New York, N.Y.

[21] Appl. No.: 633,362

[22] Filed: Apr. 16, 1996

Related U.S. Application Data

[63] Continuation-in-part of Ser. No. 458,921, Jun. 2, 1995.

[51] Int. Cl.[6] .................................................. C07D 211/06
[52] U.S. Cl. ................................ 546/205; 546/206
[58] Field of Search ................................ 546/205, 206

[56] References Cited

PUBLICATIONS

Dubocovich, et al., "Antidepressant–like activity of the melatonin receptor antagonist, luzindole (N–0774), in the mouse behavioral despair test," *European Journal of Pharmacology.*, 313–325 (1990).

*Melatonin: Biosynthesis, Physiological Effects and Clinical Applications* p. 359 (1993).

*Primary Examiner*—Amelia A. Owens
*Attorney, Agent, or Firm*—Richard P. Ryan

[57] ABSTRACT

Certain indanyl piperidines are useful as melatonergic agents and can treat various CNS disorders. They are useful in treating sleep disorders and other conditions related to circadian rhythms.

24 Claims, No Drawings

INDANYLPIPERIDINES AS MELATONERGIC AGENTS

This application is a continuation-in-part of U.S. Ser. No. 08/458,921 filed on Jun. 2, 1995.

BACKGROUND OF THE INVENTION

The invention deals with indanyl-substituted piperidines, also known in the literature as 4-(2,3-dihydro-1H-inden-1-yl)piperidines, which have bioaffecting properties and to their preparation, formulation and use. Specifically, the invention is concerned with piperidines having substituted indanyl moieties attached to the four position of the piperidine ring. These compounds are useful melatonergic agents because they are $ML_1$ receptor agonists and partial agonists. They have potential activity as sedatives, for treating sleep-related disorders and for treating anxiety, depression and various CNS disorders related to circadian rhythms.

The melatonin antagonist, luzindole, exhibits antidepressant-like effects. See Dubocovich et al, *European Journal of Pharmacology*, 182, (1990), pages 313–325. Luzindole binds to human melatonin receptors. Like luzindole, compounds of this invention bind to these receptors and, therefore, are believed to have antidepressant character. Also, low levels of melatonin have been associated with depressive disorders. See *Melatonin: Biosynthesis, Physiological Effects and Clinical Applications*, CRC Press, (1993), page 359.

Certain compounds of the invention are structurally related to compounds disclosed as intermediates in Manoury, et al., patent U.S. Pat. No. 4,963,680. See Examples 2 through 5 of the patent. However, the compounds of the '680 patent are not taught as having therapeutic activity of their own. They are only discussed as chemical intermediates in processes for making chemically distinct compounds which are therapeutic agents.

90-242933/32,EISA 22.12.88, JO 2169-569-A shows cyclic amine derivatives for the treatment or prophylaxis of senile dementia, cerebral apoplexy, cerebral atherosclerosis, traumatic cerebral damage, post cerebral edema or cerebral palsy. The compounds can be piperidines or piperazines linked to carboxamide groups and to heterocyclic rings. 89-001045/01, EISA 22.06.87, EP 296-560-A shows similar compounds having selective antiacetylcholinesterace activity.

89-074668/10, TAIY-24.07.87, JO 1029-310-A shows asthma medicaments of formula i:

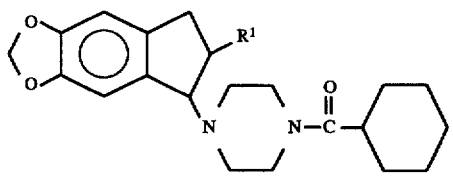

wherein $R^1$ is lower alkyl.

88-272140/39, TAIY-27.03.83, EP-283-551-A deals with drugs for amelioration of cerebral circulation and metabolism which are indene derivatives of formula ii:

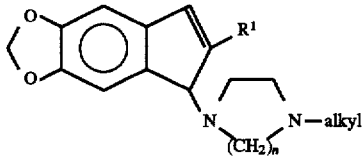

wherein $R^1$ is hydrogen or lower alkyl, and n is 2 or 3.

88-046878/07, TAIY-26.06.86, J6 3005-063-A refers to indanes used to treat bronchial asthma. The compounds are of formula iii:

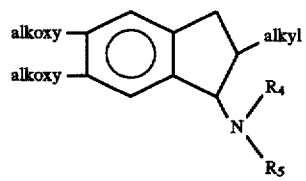

wherein $R_4$ and $R_5$ may form, with the N atom, a piperidinyl, piperazinyl or homopiperazinyl group.

U.S. Pat. No. 4,983,607 to Manoury, et al., discusses quinolinone derivatives which possess high affinity for "5-$HT_{1A}$ type serotoninergic receptors".

The structurally related compound 1-(2,3-dihydro-6-methoxy-1H-iden-1-yl)-1-homopiperazine is disclosed in Example 2 of U.S. Pat. No. 4,963,680.

WO 92/10192 of Bogeso, et al., shows compounds of formula iv:

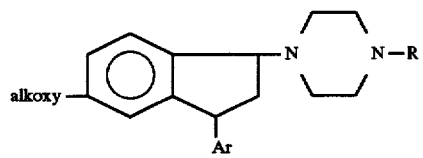

wherein Ar is an optionally substituted phenyl, thiophene or furan ring; and

R can be hydrogen, alkyl, alkenyl, cycloalkyl, or cycloalkyl-substituted alkyl.

SUMMARY AND DETAILED DESCRIPTION OF THE INVENTION

In its broadest aspect, the invention is concerned with indanyl piperidines having useful melatonergic properties, their preparation, and methods and compositions which employ them.

The compounds of the invention are those of Formula I. Formula I is:

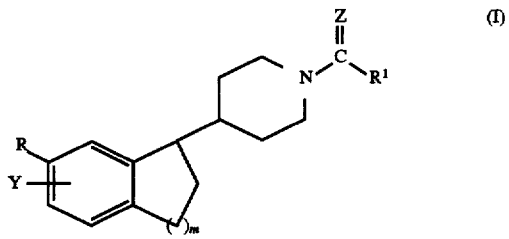

wherein:

R is H, $C_{1-7}$ alkyl, $C_{1-7}$ alkoxy, halogen, hydroxyl, $C_{1-4}$ haloalkoxy or $C_{1-4}$ alkoxyphenyl $C_{1-7}$ alkoxy;

Y is hydrogen or halogen;

Z is O or S;

m is 1 or 2; and $R^1$ is hydrogen, $C_{1-6}$ alkyl (straight or branched), $C_{1-6}$ haloalkyl (straight or branched), $C_{2-8}$ alkylthioalkyl, $C_{2-8}$ alkyloxyalkyl, $C_{2-6}$ alkenyl (straight or branched), $C_{3-5}$ cycloalkyl, $C_{3-5}$ cycloalkenyl, thienyl, furanyl, thiadiazolyl, pyrrolyl, $C_{1-6}$ alkylthio or $NR^2R^3$, in which $R^2$ and $R^3$ are independently hydrogen or $C_{1-4}$ alkyl.

Pharmaceutically acceptable mixtures of these compounds can be used.

The compounds of the invention are advantageous in several ways. They have melatonergic and other CNS properties and are believed useful as agents for the treatment of stress, sleep disorders, seasonal depression, appetite regulation, shifts in circadian cycles (e.g. jet lag), melancholia and the like.

In addition, their physical and pharmacological properties make them candidates for delivery via oral, sublingual, transnasal, transdermal, injectable, etc., dosage forms.

In Formula I:

R is H, $C_{1-7}$ alkyl, $C_{1-7}$ alkoxy, halogen, hydroxyl, $C_{1-4}$ haloalkoxy or $C_{1-4}$ alkoxyphenyl $C_{1-7}$ alkoxy.

Y is hydrogen or halogen, preferably hydrogen.

m is 1 or 2, with 1 preferred.

$R^1$ may be hydrogen, straight or branched $C_{1-6}$ alkyl, straight or branched $C_{1-6}$ haloalkyl, $C_{1-6}$ alkylthioalkyl, $C_{2-8}$ alkyloxyalkyl, straight or branched $C_{2-6}$ alkenyl, $C_{3-5}$ cycloalkyl, thienyl, furanyl, thiadiazolyl, pyrrolyl or $NR^2R^3$ group, in which $R^2$ and $R^3$ are hydrogen or $C_{1-4}$ alkyl. Alkyl, furanyl, pyrrolyl and thienyl $R^1$ moieties may have one or more $C_{1-4}$ alkyl, halogen or $C_{1-4}$ alkoxy substituents.

By "alkyl" applicants mean saturated acyclic moieties containing the indicated number of carbon atoms. They may be straight or branched.

In this disclosure, "Me", "Et", "n-Pr", "i-Pr", and "c-Pr" refer to $CH_3$—, $CH_3CH_2$—, $CH_3CH_2CH_2$—, $(CH_3)_2CH$—, and

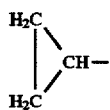

groups, respectively.

The term "alkoxy" means alkyloxy or —O-alkyl groups containing the indicated number of carbon atoms. "MeO" stands for methoxy.

When "halogen" or "halo" is used, it means a bromine, chlorine, fluorine or iodine atom.

"Hydroxyl" refers to the group, —OH.

Applicants intend "$C_{1-4}$ haloalkoxy" to mean alkoxy groups containing 1 to 4 carbon atoms and 1 to 3 halogen substituents. Trifluoromethyl is preferred.

By "haloalkyl" is meant straight or branched chain saturated alkyl groups containing 1 to 6 carbons and 1 to 12 halogen atoms.

By "alkenyl" is meant hydrocarbon moieties having from 2 to 4 carbon atoms and containing one site of ethylenic unsaturation.

The term "cycloalkyl" refers to saturated cyclic hydrocarbon groups conforming to the formula $C_xH_{(2x-1)}$ and containing from 3 to 5 carbon atoms.

The word "cycloalkenyl" means cyclic hydrocarbon, moieties containing from 3 to 5 carbon atoms and one site of ethylenic unsaturation.

"$NR^2R^3$" refers to monoalkyl- and dialkyl-amino groups wherein $R^2$ and $R^3$ are independently hydrogen or noncyclic, straight or branched $C_{1-4}$ alkyl groups. Groups wherein $R^2$ is straight or branched $C_{1-4}$ alkyl and $R^3$ is hydrogen are preferred.

When $R^1$ is a heterocyclic group (i.e., thienyl, furanyl, thiadiazolyl or pyrrolyl), it may have one or more $C_{1-4}$ alkyl, $C_{1-4}$ alkoxy and/or halogen substituent(s) on the ring. Thus methylthienyl, halothienyl, methylfuranyl and methylpyrrolyl groups are contemplated.

It is preferred that when $R^1$ is a cyclic hydrocarbon group, it have no substituents on the ring.

Preferred classes of compounds of Formula I are compounds in which R is methoxy, (Y is preferably halogen, preferably F, or hydrogen) and $R^1$ is hydrogen, $C_{1-4}$ alkyl, $C_{3-6}$ cycloalkyl, $C_{1-4}$ haloalkyl, thienyl, furanyl, thiadiazolyl and pyrrolyl and $NHR^2$, with $R^2$ being straight or branched $C_{1-4}$ alkyl. Alkyl (preferably methyl) and halogen (preferably chloro or fluoro) substituents may be on the $R^1$ groups. Salts of these are also useful.

It is highly preferred that R be the methyl substituent of a methoxy group at the 6-position and that Y be a hydrogen or F atom at the 5 position.

Compounds of Formula I also encompass all pharmaceutically acceptable solvates, particularly, hydrates, thereof. The present invention also encompasses stereoisomers as well as optical isomers, e.g., mixtures of enantiomers as well as individual enantiomers and diasteriomers, which arise as a consequence of structural asymmetry in certain compounds of Formula I and their salts. Separation of the individual enantiomers is accomplished by the use of various methods which are well known to practitioners in the art.

Preferred compounds include:

1-(Cyclopropylcarbonyl)-4-(indan-1-yl)piperidine;
1-Cyclopropylcarbonyl-4-(6-methoxy-indan-1-yl) piperidine;
4-(6-methoxy-indan-1-yl)-1-(2-methylpropanoyl) piperidine;
4-(6-Methoxy-indan-1-yl)-1-(2-methylbutanoyl)piperidine;
4-(6-Methoxy-indan-1-yl)-1-(2-methylthioacetyl) piperidine;
1-[(Cyclopent-1-en-1-yl)carbonyl]-4-(6-methoxy-indan-1-yl)piperidine;
(−)-4-(6-methoxy-indan-1-yl)-1-(trifluoroacetyl)piperidine;
4-(6-methoxy-indan-1-yl)-1-(trifluoroacetyl)piperidine;
(−)-1-Formyl-4-(6-methoxy-indan-1-yl)piperidine;
1-Formyl-4-(6-methoxy-indan-1-yl)piperidine;
(−)-1-(Cyclopropylcarbonyl)-4-(6-methoxy-indan-1-yl) piperidine;
(+)-1-(Cyclopropylcarbonyl)-4-(6-methoxy-indan-1-yl) piperidine;
4-(6-Methoxy-indan-1-yl)-1-(2-methoxy-acetyl)piperidine;
(−)-4-(6-Methoxy-indan-1-yl)-1-(2-methoxyacetyl) piperidine;
(−)-4-(6-Methoxy-indan-1-yl)-1-(2-methyl-propanoyl) piperidine;
1-(Cyclopropylcarbonyl)-4-(5-fluoro-6-methoxy-indan-1-yl)piperidine;
4-(5-Fluoro-6-methoxy-indan-1-yl)1-(2-methylpropanoyl) piperidine;
(−)-4-(6-Methoxy-indan-1-yl)-1-pentanoylpiperidine;
(−)-1-Butanoyl-4-(6-methoxy-indan-1-yl)piperidine;
(−)-4-(6-Methoxy-indan-1-yl)-1-propanoylpiperidine;
(−)-1-Acetyl-4-(6-methoxy-indan-1-yl)piperidine;
1-Butanoyl-4-(5-fluoro-6-methoxy-indan-1-yl)piperidine;
4-(5-Fluoro-6-methoxy-indan-1-yl)-1-propanoylpiperidine;
1-Acetyl-4-(5-fluoro-6-methoxy-indan-1-yl)piperidine;
1-(Cyclopropylcarbonyl)-4-(6-fluoro-indan-1-yl)piperidine;
4-(6-Fluoro-indan-1-yl)-1-(2-methylpropanoyl)piperidine;
1-Butanoyl-4-(6-fluoro-indan-1-yl)piperidine;
4-(6-Ethyl-indan-1-yl)-1-(2-methylpropanoyl)piperidine;
1-(Cyclopropylcarbonyl)-4-(6-ethyl-indan-1-yl)piperidine;
1-(Cyclopropylcarbonyl)-4-[6-[3-(3-methoxyphenyl) propyloxy]-indan-1-yl]piperidine;
1-(2,2-Dimethyl-butanoyl)-4-(6-methoxy-indan-1-yl) piperidine;

(+)-4-(6-Methoxy-indan-1-yl)-1-(trifluoroacetyl)piperidine;
(+)-1-Formyl-4-(6-methoxy-indan-1-yl) piperidine;
(+)-4-(6-Methoxy-indan-1-yl)-1-(2-methylpropanoyl) piperidine;
N-(Cyclopropylcarbonyl)-4-(6-hydroxy-indan-1-yl) piperidine;
1-(Cyclopropylcarbonyl)-4-[6-(trifluoromethoxy)-indan-1-yl]piperidine;
(+)-1-(2-Methoxyacetyl)4-(6-methoxy-indan-1-yl) piperidine;
4-(6-Methoxy-indan-1-yl)-1-[(2-thienyl)carbonyl] piperidine;
1-[(2-Furanyl)carbonyl]-4-(6-methoxy-indan-1-yl)-piperidine;
4-(6-Methoxy-indan-1-yl)-1-[(1H-pyrrol-2-yl)carbonyl] piperidine;
4-(6-Methoxy-indan-1-yl)-1-[(3-methyl-furan-2-yl)carbonyl]piperidine;
1-[(3-Furanyl)carbonyl]4-(6-methoxy-indan-1-yl)-piperidine;
4-(6-Methoxy-indan-1-yl)-1-[(1-methyl-pyrrol-2-yl)carbonyl]piperidine;
4-(6-Methoxy-indan-1-yl)-1-[(3-methyl-thien-2-yl)carbonyl]piperidine;
4-(6-Methoxy-indan-1-yl)-1-[(3-thienyl)carbonyl] piperidine;
1-[(3-Chloro-thien-2-yl)carbonyl]-4-(6-methoxy-indan-1-yl)-piperidine;
4-(6-Methoxy-indan-1-yl)-1-[(1,2,3-thiadiazol-4-yl)carbonyl]piperidine;
4-(6-methoxy-indan-1-yl)-1-[(5-methyl-thien-2-yl)carbonyl]piperidine;
1-[(2-Chloro-3-methoxythien-4-yl)carbonyl]-4-(6-methoxy-indan-1-yl)piperidine;
N-Ethyl-4-(6-methoxy-indan-1-yl)piperidine-1-carboxamide;
N-Methyl-4-(6-methoxy-indan-1-yl)piperidine-1-carboxamide;
(−)-N-Ethyl-4-(6-methoxy-indan-1-yl)piperidine-1-carboxamide;
(−)-N-Methyl-4-(6-methoxy-indan-1-yl)piperidine-1-carboxamide;
(−)-N,N-Dimethyl-4-(6-methoxy-indan-1-yl)piperidine-1-carboxamide;
N-Methyl-4-(5-fluoro-6-methoxy-indan-1-yl)piperidine-1-carboxamide;
N-Ethyl-4-(6-fluoro-indan-1-yl)piperidine-1-carboxamide;
N-Ethyl-4-(6-ethyl-indan-1-yl)piperidine-1-carboxamide;
N-Ethyl-4-[6-(n-heptyloxy)-indan-1-yl]piperidine-1-carboxamide;
N-Methyl-4-(6-methoxy-indan-1-yl)-piperidine-1-thiocarboxamide;
N-Methyl-4-(indan-1-yl)-piperidine-1-carboxamide;
N-Ethyl-4-[6-[3-(3-methoxyphenyl)propyloxy]-indan-1-yl] piperidine-1-carboxamide;
N-Ethyl-4-(indan-1-yl)-piperidine-1-carboxamide;
(+)N-Ethyl-4-(6-methoxy-indan-1-yl)piperidine-1-carboxamide;
(+)-N-Methyl-4-(6-methoxy-indan-1-yl)piperidine-1-carboxamide;
N-Ethyl-4-(5-fluoro-6-methoxy-indan-1-yl)piperidine-1-carboxamide;
N-Methyl-4-(6-fluoro-indan-1-yl)piperidine-1-carboxamide;
N-Ethyl-4-[6-(trifluoromethoxy)-indan-1-yl]piperidine-1-carboxamide;
1-(Cyclopropylcarbonyl)-4-(7-methoxy-tetralin-1-yl) piperidine; and
N-Ethyl-4-(7-methoxy-tetralin-1-yl)piperidine-1-carboxamide.

Compounds of Formula I can be prepared using the processes shown in the following schemes:

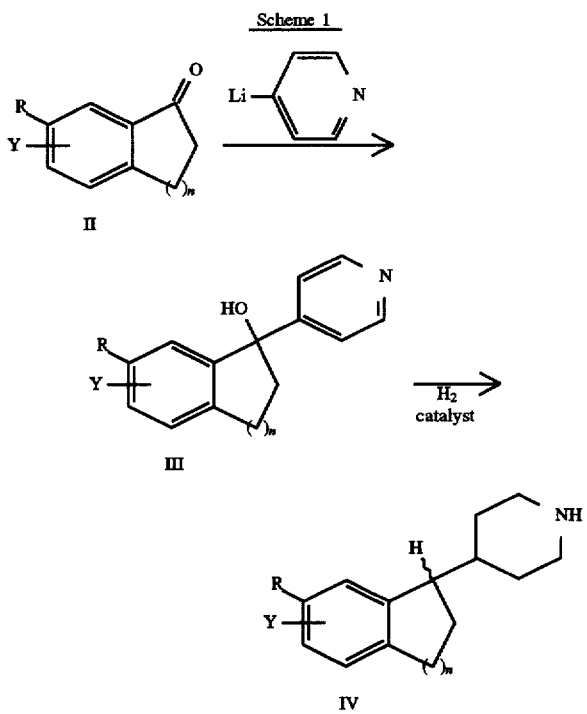

The synthesis of the piperidine intermediates is shown in Scheme 1. The starting ketones, II, can be prepared by methods well known to those skilled in the art. Addition of 4-pyridinyl lithium to the ketones, II, in solvents such as diethyl ether gives the pyridinyl-alcohol intermediates, III. Subsequent hydrogenation of these intermediates, III, with catalysts such as platinum oxide provides the intermediate piperidines, IV, in good yields. Resolution of the enantiomers of the piperidines, IV, can be accomplished by standard methods well known to those skilled in the art, such as recrystallization the tartrate salts as shown in Scheme 2.

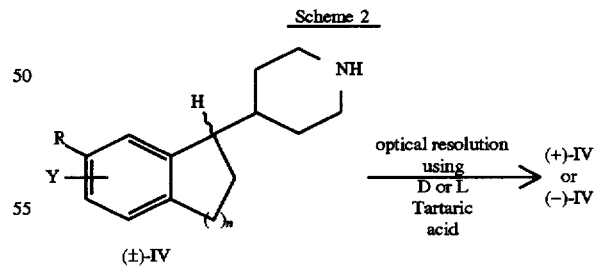

The intermediate piperidines, IV, either racemic or optically active, can be converted (Scheme 3) to compounds of Formula I, by condensation with acylating agents such as carboxylic acid halides, carboxylic acid anhydrides, alkyl isocyanates, alkyl isothiocyanates, or carboxylic acids in the presence of condensing agents such as carbonyl diimidazole, carbodiimides, or the like, under standard conditions known to those skilled in the art.

Scheme 3

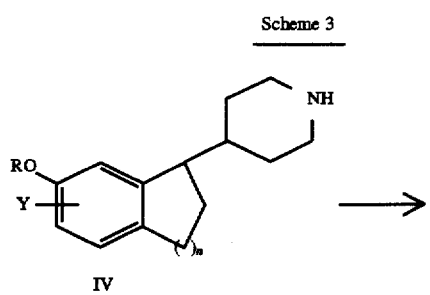

IV

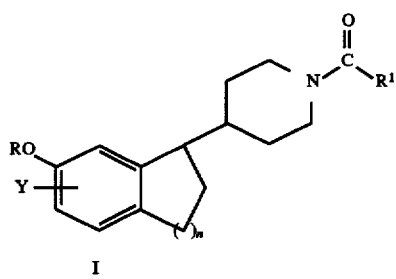

I

In those compounds of Formula I, where R is a methyl group, the methyl group may be cleaved (Scheme 4) to give the compounds of Formula I, where R is a hydrogen. Suitable reagents for this cleavage include boron tribromide, trimethylsilyl iodide, or the like, under conditions known to those skilled in the art. Subsequent alkylation of I (R=H) using alkyl iodides and the like, with bases such as NaOH, KOH, $Na_2CO_3$, or $K_2CO_3$, in suitable solvents, can provide compounds of Formula I, where R is larger than methyl.

Scheme 4

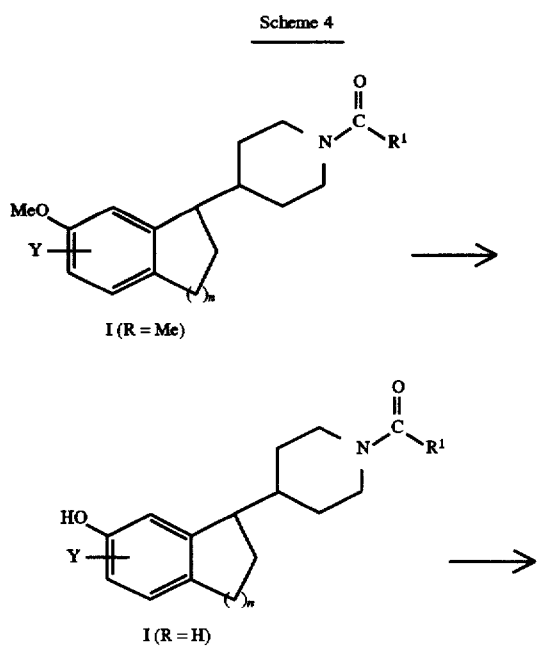

-continued
Scheme 4

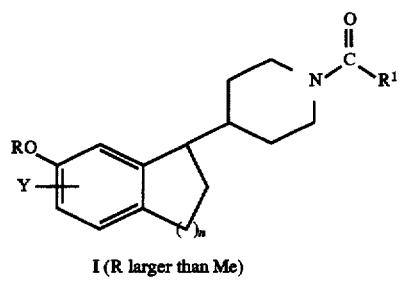

I (R larger than Me)

These processes may be adapted in order to produce other compounds embraced by the invention, but not specifically disclosed herein. Variations of these methods to produce compounds via different, but conventional, routes will be evident to one skilled in the art. Representative examples are set out in "Description of Specific Embodiments" section, below.

The compounds of the invention may be administered to patients in need of melatonergic treatment in variety of ways. Thus oral, transdermal, subcutaneous, intravenous, intramuscular, rectal, buccal, intranasal and ocular routes can be used.

At least one of the compounds of the invention is mixed with pharmaceutically suitable amounts of one or more conventional pharmaceutical excipients to produce a formulation to be administered by the desired route. Generally, such formulations will contain one or several carriers or diluents. Useful carriers include solids, semi-solids, and liquids which have miscibility, or other compatability, with the active agents(s) so the they can efficiently deliver same to a patient or other host.

Suitable carriers include lactose, dextrose, sucrose, sorbitol, mannitol, starches, gum acacia, calcium phosphate, alginates, tragacanth, gelatin, calcium silicate, microcrystalline cellulose, polyvinyl pyrrolidone, cellulose, water, syrup, methyl cellulose, methyl- and propylhydroxybenzoates, talc, magnesium stearate, mineral oil and the like. Mixtures are operable.

Other useful excipients include, lubricants, wetting agents, gellants, emulsifiers, preservatives, colorants, perfumes, flavor enhancers, drying agents and the like. Mixtures can be employed.

Generally, compositions which include the compounds of the invention will contain form about 0.10 to about 10% by weight of active compound(s) and 99.9 to 90% by weight, or other suitable amounts, of excipients(s).

Dosage levels will be dictated by the patient's needs and by the medical judgment of the treating physician. Generally, however, dosages of about 0.1 to about 100 mg per day are useful to treat sleep disorders, depression, or other disorders related to circadian rhythm.

While human patients are preferred, the compounds of the invention may be used to treat other subjects, i.e., animals, preferably mammals.

DESCRIPTION OF SPECIFIC EMBODIMENTS

The compounds of the invention, their preparation and their biological properties will be more clearly understood upon consideration of the following examples. The

9 examples are illustrative only and are not intended to limit the scope the invention.

In these examples, temperatures are expressed in degrees Celsius and melting points are uncorrected. The nuclear magnetic resonances (NMR) are spectral characteristics, referring to chemical shifts (δ) expressed as parts per million (ppm) versus tetramethylsilane (TMS) as reference standard. The relative area reported for the various shifts in the $^1$H NMR spectral data corresponds to the number of hydrogen atoms of a particular functional type in the molecule. The nature of the shifts as to multiplicity is reported as a broad singlet (bs), singlet (s), multiplet (m) or doublet (d).

Abbreviations employed are DMSO-$d_6$ (deuterodimethylsulfoxide), CDCl$_3$ (deuterochloroform) and are otherwise conventional. The infrared (IR) spectral descriptions include only absorption wave numbers (cm$^{-1}$) having functional group identification value. The IR determinations were employed using potassium bromide (KBr) as diluent. The elemental analysis results are reported as percent by weight.

All percentages are, unless less designated otherwise, weight percent based on total composition weight.

EXAMPLES

The following examples illustrate the preparation of compounds of Formula I as well as intermediates.

Example 1

4-(6-methoxy-indan-1-yl)piperidine

Step 1. 4-(1-hydroxy-6-methoxy-indan-1-yl)pyridine.

To a solution of n-butyl lithium in ether (11 mL, 22 mmol) at −78° C. was added 4-bromopyridine (3.2 g, 20 mmol). After stirring for 0.5 h, 6-methoxy-1-indanone (3.2 g, 20 mmol) was added. The mixture was stirred for 16 h during which time it was allowed to warm to room temperature. The mixture was quenched with sat'd NH$_4$Cl solution and the ether layer separated and washed with 1N HCl solution. The acid washes were made basic with 30% NaOH solution and the basic mixture was extracted with methylene chloride. The extracts were dried over Na$_2$SO$_4$ and concentrated in vacuo. The residue was crystallized from 2-propyl ether to give 2.8 g (58%) of product, mp 169°–171° C.; IR (KBr) 3100, 1602, 1280, 1494, 1030 cm$^{-1}$; $^1$H NMR (CDCl$_3$, 300 MHz) δ 8.49 (br s, 2H), 7.29 (d, 2H, J=5.6 Hz), 7.21 (d, 1H, J=8.3 Hz), 6.86 (dd, 1H, J$_1$=8.3 Hz, J$_2$=2.4 Hz), 6.51 (d, 1H, J=2.4 Hz), 3.69 (s, 3H), 3.15–3.05 (m 1H), 2.94–2.85 (m, 1H), 2.46 (t, 2H, J=7.1 Hz). Anal. Calc'd for C$_{15}$H$_{15}$NO$_2$: C, 74.67%; H, 6.27%; N, 5.80%. Found: C, 74.69%; H, 6.24%; N, 5.73%.

Step 2. 4-(6-methoxy-indan-1-yl)piperidine

A mixture of platinum oxide (0.1 g), 4-(1-hydroxy-6-methoxy-indan-1-yl)pyridine (1 g, 4.2 mmol), and 37% HCl (1 mL) was hydrogenated for 5 h. The catalyst was removed and the solution was concentrated in vacuo. The residue was recrystallized from 2-propanol to give 0.8 g (73%) of hydrochloride salt, mp 197°–198° C.; IR (KBr) 2946, 1584, 1488, 1288, 798 cm$^{-1}$; $^1$H NMR (DMSO-$d_6$, 300 MHz) δ 8.94 (br s, 1H), 8.69 (br s, 1H), 7.09 (d, 1H, J=8.2 Hz), 6.76 (d, 1H, J=2.1 Hz), 6.70 (dd, 1H, J$_1$=8.2 Hz, J$_2$=2.1 Hz), 3.70 (s, 3H), 3.22 (br t, 2H, J=14 Hz), 3.08–3.02 (m, 1H), 2.89–2.62 (m, 3H), 2.11–1.93(m, 2H), 1.86–1.77 (m, 2H), 1.57–1.45 (m, 3H). Anal. Calc'd for C$_{15}$H$_{21}$NO•HCl: C, 67.27%; H, 8.28%; N, 5.23%. Found: C, 66.91%; H, 8.33%; N, 5.19%.

10

Example 2

4-(6-Ethylindan-1-yl)piperidine

Step 1. 4-Ethyl cinnamic acid

A solution of 4-ethylbenzaldehyde (26.0 g, 0.2 mol), malonic acid (41.6 g, 0.4 mol), pyrrolidine (3 ml), and pyridine (80 ml) was heated in an 85° C. oil bath for 16 hr. The reaction mixture was poured over crushed ice (800 ml), and then made acidic with 12N HCl (100 ml). The white precipitate was filtered, suspended in 1N HCl, and filtered again. The white precipitate was washed with water and air dried to give 4-ethyl cinnamic acid (34.0 g, 96.6%).

Step 2. 3-(4-Ethylphenyl)propionic acid

An ethanol (250 ml) solution of 4-ethyl cinnamic acid (34.0 g, 0.191 mol) was hydrogenareal at 60 psi over 10% Pd/C (2 g) for 2 hr. The mixture was filtered and concentrated in vacuo to give 3-(4-ethylphenyl)propionic acid as a white solid (34 g, 100%).

Step 3. 6-Ethyl-1-indanone

A mixture of 3-(4-ethylphenyl)propionic acid (34 g, 0.191 mol) and thionyl chloride (70 ml), and CH$_2$Cl$_2$ (100 ml) was heated to reflux for 30 min. The resulting solution was concentrated in vacuo to a light brown oil. This oil was added slowly to an ice bath cooled mixture of AlCl$_3$ (33.1 g, 0.248 mole) in CH$_2$Cl$_2$ (75 ml). The mixture was stirred for 15 min and then heated to reflux for 45 min. The mixture was cooled and poured over crushed ice (200 ml) and 12N HCl (100 ml). The CH$_2$Cl$_2$ layer was separated, washed with 3N HCl, saturated Na$_2$CO$_3$, water, and brine. The CH$_2$Cl$_2$ layer was concentrated in vacuo and Kügelrohr distilled to a clear oil (27.4 g, 89%). $^1$H-NMR (CDCl$_3$, 300 MHz) δ 1.23 (t, 3H, J=7.5 Hz), 2.65–2.72 (m, 4H),3.07 (t, 2H, J=5.9 Hz), 7.36 (d, 1H, J=8.1 Hz), 7.41 (d, 1H, J=8.1 Hz), 7.57 (s, 1H).

Step 4. 4-(6-Ethyl-indan-1-yl)piperidine

The 6-ethyl-1-indanone was converted to 4-(6-ethyl-indan-1-yl)piperidine by the method given in Example 1 above, mp 153°–155° C. (fumarate salt); IR (KBr) 2962, 1738, 1568, 1316, 642 cm$^{-1}$; $^1$H NMR (DMSO-$d_6$, 300 MHz) δ 7.12 (bs, 1H), 3.24 (t, 3H, J=12.11 Hz), 3.04 (m, 1H), 2.81–2.72 (m, 6H), 2.58 (q, 2H, J=7.5 Hz), 2.09–2.02 (m, 1H), 1.93–1.80 (m, 2H), 1.74 (bd, J=13 Hz), 1.48 (m, 2H), 1.16(t, 3H, J=7.5 Hz). Anal. Calc'd for C$_{16}$H$_{23}$N•C$_4$H$_4$O$_4$•0.2H$_2$O: C, 68.47%; H, 7.93%; N, 3.99%. Found: C, 68.46%; H, 7.73%; N, 4.08%.

Example 3

4-(6-(trifluoromethoxy)indan-1-yl)piperidine

4-Trifluoromethoxybenzaldehyde was converted to 6-(trifluoromethoxy)-1-indanone as described above in Example 2, steps 1–3 for 6-ethylindanone. The product was purified by silica chromatography eluting with ethyl acetate-hexane (1:99); MS m/e 216M$^+$. The indanone was converted to 4-(6-trifluoromethoxy-1-indanyl)piperidine as described in step 4 above, MS m/e 285M$^+$.

Example 4

4-(6-fluoro-indan-1-yl)piperidine

This compound was prepared in two steps from 4-bromopyridine and 5-fluoro-6-methoxy-1-indanone as described in method 2 above to give the product as the HCl salt (66%, mp: 178°–179° C.). Anal. Calc'd for C$_{15}$H$_2$FNO•HCl: C, 63.04%; H, 7.41%; N, 4.90%. Found: C, 62.80%; H, 7.30%; N, 4.70%.

Example 5

4-(6-(3-(3-methoxyphenyl)prop-1-yl)oxy)indan-1-yl)piperidine

This compound was prepared from 4-bromopyridine and 6-(3-(3-methoxyphenyl)prop-1-yl)oxy)indan-1-one in two steps as described above in method 2 to give the product as an oil (48%).

Example 6

4-(indan-1-yl)piperidine

This compound was prepared from 4-bromopyridine and 1-indanone in two steps as described above in method 2 to give the product as the HCl salt [96%, mp: 205° C. (dec)]

Example 7

Resolution of 4-(6-methoxy-indan-1-yl)piperidine, IV.

(+)-4-(6-methoxy-indan-1-yl)piperidine

A mixture of 4-(6-methoxy-indan-1-yl)piperidine (8.4 g, 36.4 mmol) and L-tartaric acid (2.7 g, 18.2 mmol) was dissolved in 150 mL ethanol-water (10:1). After standing for 5 h the precipitate was collected and recrystallized from 50 mL ethanol-water (10:1) to give of (+)-4-(6-methoxy-indan-1-yl)piperidine L-tartrate (2.0 g, 18%), mp 183°–184° C., [α]=53.4°. Anal. Calc'd for $C_{15}H_{21}NO_2 \cdot C_4H_6O_6$: C, 59.83%; H, 7.14%; N, 3.68%. Found: C, 59.83%; H, 7.21%; N, 3.66%. A sample of the hydrochloride was prepared in ethanol, mp 168°–169° C., [α]=57.2°. Anal. Calc'd for $C_{15}H_{21}NO_2 \cdot HCl$: C, 67.28%; H, 8.28%; N, 5.23%. Found: C, 67.20%; H, 8.30%; N, 5.11%.

(−)-4-(6-methoxy-indan-1-yl)piperidine

The mother liquors were concentrated in vacuo and the residue made basic. The mixture was extracted with ether and the extracts concentrated in vacuo to give 6.5 g (28 mmol) of oil. The oil was dissolved in 75 mL ethanol-water (10:1) with 2.1 g (14 mmol) D-tartaric acid and allowed to stand to give 2.0 g of solid. Recrystallization from 50 mL ethanol-water (10:1) gave 1.6 g (14%) (−)-4-(6-methoxy-indan-1-yl)piperidine D-tartrate, mp 223°–224° C., [α]=−59.2°. Anal. Calc'd for $C_{15}H_{21}NO_2 \cdot C_4H_6O_6$: C, 59.83%; H, 7.14%; N, 3.68%. Found: C, 59.58%; H, 7.13%; N, 3.59%. A sample of the hydrochloride was prepared in ethanol, mp 168°–169° C., [α]=−55.4°. Anal. Calc'd for $C_{15}H_{21}NO_2 \cdot HCl \cdot H_2O$: C, 65.51%; H, 8.36%; N, 5.09%. Found: C, 65.57%; H, 8.10%; N, 4.97%.

Example 8

General Procedure for Preparation of Ureas of Formula I

N-Ethyl-4-(6-methoxy-indan-1-yl)-1-piperidinecarboxamide

Ethyl isocyanate (0.14 g, 2 mmol) was added to a solution of 4-(6-methoxy-indan-1-yl)piperidine (0.46 g, 2 mmol) in $CH_2Cl_2$ and the solution was stirred for 72 h. The solution was concentrated in vacuo and the residue crystallized from 2-propyl ether to give the product (0.35 g, 56%), mp 183°–184° C.; IR (KBr) 3360, 1616, 1542, 1488, 1244 cm$^{-1}$; $^1$H NMR (CDCl$_3$, 300 MHz) δ 7.08 (d, 1H, J=7.7 Hz), 6.69–6.66 (m, 2H), 4.34 (br m, 1H), 4.00–3.84 (m, 2H), 3.77 (s, 3H), 3.28–3.18 (m, 2H), 3.06–3.01 (m, 1H), 2.79–2.59 (m, 4H), 2.11–2.05(m, 1H), 1.90–1.76 (m, 2H), 1.68–1.65 (m, 1H), 1.46–1.18 (m, 3H), 1.10 (1, 3H. J=7.2 Hz). Anal. Calc'd for $C_{18}H_{26}N_2O_2$: C, 71.49%; H, 8.67%; N, 9.26%. Found: C, 71.39%; H, 8.37%; N, 9.24%.

Table 1 lists additional compounds of Formula I that were prepared by this method.

TABLE 1

| +/− | R | Y | Z | m | R$^1$ | IR νCO cm$^{-1}$ | yield % | empirical formula | Calcd %C | Found %C | %H | %N |
|---|---|---|---|---|---|---|---|---|---|---|---|---|
| ± | Et | H | O | 1 | —NHEt | 1624 | 60 | $C_{19}H_{29}N_2O$ | 75.96 | 75.80 | 9.39 / 9.23 | 9.32 / 9.35 |
| ± | F | H | O | 1 | —NHEt | 1622 | 64 | $C_{17}H_{23}FN_2O \cdot 0.35 CH_2Cl_2$ | 65.55 | 65.45 | 7.37 / 7.48 | 8.64 / 9.02 |
| ± | F | H | O | 1 | —NHMe | 1624 | 97 | $C_{16}H_{21}FN_2O \cdot 0.4 H_2O$ | 67.77 | 67.71 | 7.75 / 7.45 | 9.88 / 10.14 |
| ± | F$_3$CO— | H | O | 1 | —NHEt | 1616 | 56 | $C_{18}H_{23}F_3N_2O_2$ | 60.66 | 60.64 | 6.50 / 6.12 | 7.86 / 7.76 |
| + | MeO— | H | O | 1 | —NHEt | 1622 | 66 | $C_{18}H_{26}N_2O_2 \cdot 0.8 H_2O$ | 68.24 | 67.86 | 8.78 / 8.50 | 8.84 / 9.40 |
| + | MeO— | H | O | 1 | —NHMe | 1624 | 86 | $C_{17}H_{24}N_2O_2 \cdot 0.2 H_2O$ | 69.93 | 70.01 | 8.42 / 8.51 | 9.60 / 9.59 |
| ± | MeO— | H | O | 1 | —NHEt | 1620 | 94 | $C_{18}H_{25}N_{22}$ | 67.48 | 67.23 | 7.86 / 8.09 | 8.74 / 8.58 |
| − | MeO— | H | O | 1 | NHEt | 1622 | 78 | $C_{18}H_{26}N_2O_2 \cdot 0.5 H_2O$ | 69.42 | 69.59 | 8.74 / 8.53 | 9.00 / 9.01 |
| ± | MeO— | H | O | 1 | —NHMe | 1624 | 100 | $C_{17}H_{24}NO_2 \cdot 0.55 H_2O$ | 68.45 | 68.18 | 8.48 / 8.54 | 9.39 / 10.12 |
| − | MeO— | H | O | 1 | —NHMe | 1624 | 93 | $C_{17}H_{24}N_2O_2$ | 69.93 | | 8.42 | 9.6 |

TABLE 1-continued

[Structure: indane ring with R and Y substituents, connected to piperidine with N-C(=O)-R¹ group, (CH₂)ₘ]

| +/- | R | Y | Z | m | R¹ | IR νCO cm⁻¹ | yield % | empirical formula | Calcd / Found %C | %H | %N |
|---|---|---|---|---|---|---|---|---|---|---|---|
| − | MeO— | H | O | 1 | —NMe₂ | 1646 | 99 | C₁₈H₂₆N₂O₂· 0.2 H₂O | 69.94 / 69.42 | 8.59 / 8.74 | 9.61 / 9.00 |
| ± | MeO— | H | O | 2 | —NHEt | 1618 | 79 | C₁₉H₂₈N₂O₂ 0.15 H₂O | 69.34 / 72.12 / 72.01 | 8.51 / 8.92 / 8.92 | 8.84 / 8.85 / 8.65 |
| ± | MeO— | 5-F | O | 1 | —NHEt | 1620 | 94 | C₁₈H₂₅FN₂O₂ | 67.48 / 67.23 | 7.82 / 8.09 | 8.74 / 8.58 |
| ± | MeO— | 5-F | O | 1 | —NHMe | 1626 | 85 | C₁₈H₂₅FN₂O· 0.1 H₂O | 66.26 / 66.14 | 7.59 / 7.61 | 9.09 / 9.12 |
| ± | 3-OMe-Ph—(CH₂)₃O— | H | O | 1 | —NHEt | 1620 | 64 | C₂₇H₃₆N₂O₃ | 71.19 / 71.32 | 7.92 / 8.03 | 6.02 / 5.96 |
| ± | n-C₇H₁₅O— | H | O | 1 | —NHEt | 1623 | 88 | C₂₄H₃₈N₂O₂ | 71.63 / 71.63 | 9.45 / 9.62 | 6.82 / 6.97 |
| ± | MeO— | H | S | 1 | —NHMe | 1535 | 66 | C₁₇H₂₄N₂OS· 0.05 CH₂Cl₂ | 66.40 / 66.49 | 7.85 / 7.87 | 9.06 / 9.16 |
| ± | H— | H | O | 1 | —NHMe | 1624 | 89 | C₁₆H₂₂N₂O· 0.2 CH₂Cl₂ | 70.23 / 69.83 | 8.16 / 8.08 | 9.99 / 10.40 |
| ± | H— | H | O | 1 | —NHEt | 1623 | 16 | C₁₇H₂₄N₂O· 0.2 CH₂Cl₂ | 71.62 / 71.75 | 8.43 / 8.79 | 9.60 / 9.75 |

Example 9

General Procedures for Preparation of Amides
N-Cyclopropylcarbonyl-4-(-6-methoxy-indan-1-yl)piperidine A mixture of 4-(6-methoxy-indan-1-yl)piperidine (0.46 g, 2 mmol), cyclopropane carbonyl chloride (0.21 g, 2 mmol), and excess powdered potassium carbonate in acetonitrile was stirred for 72 h. The solution was filtered and concentrated in vacuo. The residue chromatographed on silica eluting with 2% methanol in methylene chloride to give, on concentration of the appropriate fractions, the product as an oil (0.5 g, 83%), IR (KBr) 2940, 1636, 1490, 1244, 1034 cm⁻¹; H NMR (CDCl₃, 300 MHz) δ 7.08 (d, 1H, J=7.9 Hz), 6.70–6.67 (m, 2H), 5.27 (m, 2H), 3.77 (s, 3H), 3.10–3.04 (m, 1H), 2.83–2.67 (m, 4H), 2.13–2.03 (m, 1H), 1.92–1.83 (m, 2H), 1.75–1.67 (m, 2H), 1.52–1.48 (m, 1H), 1.37–1.18 (m, 2H), 0.96–0.91 (m,2H), 0.73–0.67 (m, 2H). Anal. Calc'd for C₁₉H₂₅NO₂·0.2CH₂Cl₂: C, 73.08%; H, 8.03%; N, 4.39%. Found: C, 72.81%; H, 7.94%; N, 4.44%.

Table 2 lists additional compounds of Formula I theft were prepared by this method.

TABLE 2

[Structure: indane ring with R and Y substituents, connected to piperidine with N-C(=O)-R¹ group, (CH₂)ₙ]

| +/- | R | Y | m | R¹ | IR νCO cm⁻¹ | yield (%) | empirical formula | Calcd / Found %C | %H | %N |
|---|---|---|---|---|---|---|---|---|---|---|
| ± | Et— | H— | 1 | -c-Pr | 1638 | 82 | C₂₀H₂₇NO | 79.56 / 79.47 | 9.18 / 9.00 | 4.64 / 4.36 |
| ± | Et— | H— | 1 | -i-Pr | 1644 | 62 | C₂₀H₂₉NO | 80.22 / 79.94 | 9.76 / 9.80 | 4.68 / 4.86 |
| ± | F— | H— | 1 | -c-Pr | 1634 | 70 | C₁₈H₂₂FNO· 0.2 H₂O | 74.30 / 74.20 | 7.76 / 7.69 | 4.81 / 4.77 |

TABLE 2-continued

[Structure: indane fused with substituents R, Y, (CH2)n, connected to a piperidine ring bearing N-C(=O)-R¹]

| +/- | R | Y | m | R¹ | IR νCO cm⁻¹ | yield (%) | empirical formula | Calcd Found %C | %H | %N |
|---|---|---|---|---|---|---|---|---|---|---|
| ± | F— | H— | 1 | -i-Pr | 1638 | 70 | $C_{18}H_{24}FNO$. 0.2 $H_2O$ | 73.79 73.68 | 8.40 8.25 | 4.78 4.75 |
| ± | F— | H— | 1 | -n-Pr | 1640 | 70 | $C_{18}H_{24}FNO$. 0.2 $H_2O$ | 73.79 73.88 | 8.40 8.36 | 4.78 4.74 |
| ± | F₃CO— | H— | 1 | -c-Pr | 1638 | 43 | $C_{19}H_{22}F_3NO_2$ | 64.58 64.35 | 6.27 5.96 | 3.96 3.92 |
| ± | MeO— | H— | 1 | —CF₃ | 1692 | 45 | $C_{17}H_{20}NO_2$ | 62.38 62.14 | 6.16 6.08 | 4.28 4.24 |
| — | MeO— | H— | 1 | —CF₃ | 1692 | 47 | $C_{17}H_{20}F_3NO_2$ | 62.38 62.54 | 6.16 6.33 | 4.28 4.25 |
| ± | MeO— | H— | 1 | —CF₃ | 1692 | 71 | $C_{17}H_{20}F_3NO_2$ | 62.38 62.14 | 6.16 6.08 | 4.26 4.24 |
| ± | MeO— | H— | 1 | —CH₂OMe | 1646 | 33 | $C_{18}H_{25}NO_3$. 0.2 $H_2O$ | 70.42 70.49 | 8.34 8.34 | 4.56 4.42 |
| — | MeO— | H— | 1 | —CH₂OMe | 1646 | 78 | $C_{18}H_{25}NO_3$. 0.4 $H_2O$ | 69.60 69.60 | 8.37 8.22 | 4.51 4.45 |
| + | MeO— | H— | 1 | —CH₂OMe | 1645 | 99 | $C_{18}H_{25}NO_3$. 1.0 $H_2O$ | 67.26 67.20 | 8.47 8.09 | 4.36 4.36 |
| — | MeO— | H— | 1 | -c-Pr | 1636 | 92 | $C_{19}H_{25}NO_2$. 0.2 $H_2O$ | 75.31 75.55 | 8.45 8.57 | 4.62 4.56 |
| + | MeO— | H— | 1 | -c-Pr | 1636 | 25 | $C_{19}H_{25}NO_2$. 0.2 $H_2O$ | 75.31 75.44 | 8.45 8.4 | 4.62 4.59 |
| — | MeO— | H— | 1 | —Et | 1642 | 91 | $C_{18}H_{25}NO_2$. 0.4 $H_2O$ | 73.38 73.59 | 8.83 8.67 | 7.76 4.62 |
| — | MeO— | H— | 1 | —H | 1672 | 49 | $C_{16}H_{21}NO_2$. 0.2 $H_2O$ | 73.08 73.23 | 8.2 8.31 | 5.33 5.19 |
| + | MeO— | H— | 1 | —H | 1672 | 47 | $C_{16}H_{21}NO_2$. 0.2 $H_2O$ | 73.08 72.98 | 8.20 8.32 | 5.33 5.19 |
| ± | MeO— | H— | 1 | —H | 1672 | 42 | $C_{16}H_{21}NO_2$. 0.2 $H_2O$ | 73.08 73.03 | 8.2 8.29 | 5.33 5.22 |
| + | MeO— | H— | 1 | -i-Pr | 1642 | 99 | $C_{19}H_{27}NO_2$. 0.4 $H_2O$ | 73.94 74.03 | 9.08 9.00 | 4.45 4.38 |
| ± | MeO— | H— | 1 | -i-Pr | 1642 | 50 | $C_{19}H_{27}NO_2$. 0.2 $CH_2Cl_2$ | 69.9 70.03 | 8.24 7.97 | 4.11 4.24 |
| — | MeO— | H— | 1 | -i-Pr | 1640 | 78 | $C_{19}H_{27}NO_2$. 0.5 $H_2O$ | 73.51 73.67 | 9.09 8.98 | 4.51 4.55 |
| — | MeO— | H— | 1 | —Me | 1644 | 82 | $C_{17}H_{23}NO_2$. 0.4 $H_2O$ | 72.77 72.91 | 8.55 8.4 | 4.99 4.78 |
| — | MeO— | H— | 1 | -n-Bu | 1644 | 96 | $C_{20}H_{29}NO_2$. 0.25 $H_2O$ | 75.08 75.05 | 9.29 9.29 | 4.38 4.16 |
| — | MeO— | H— | 1 | -n-Pr | 1642 | 87 | $C_{19}H_{27}N_2O$. 0.4 $H_2O$ | 73.94 74.07 | 9.08 8.98 | 4.54 4.3 |
| ± | MeO— | H— | 2 | -c-Pr | 1636 | 64 | $C_{20}H_{27}N_2O$. 0.25 $H_2O$ | 75.55 75.61 | 8.72 8.72 | 4.41 4.24 |
| ± | MeO— | 5-F— | 1 | -c-Pr | 1636 | 88 | $C_{19}H_{24}FNO_2$ | 71.9 71.65 | 7.62 7.75 | 4.41 4.17 |
| ± | MeO— | 5-F— | 1 | —Et | 1642 | 67 | $C_{18}H_{24}FN_2O$ 0.5 $H_2O$ | 68.76 68.94 | 8.02 7.8 | 4.45 4.17 |
| ± | MeO— | 5-F— | 1 | -i-Pr | 1642 | 88 | $C_{19}H_{26}FNO_2$. 0.15 $H_2O$ | 70.84 70.84 | 8.23 8.32 | 4.35 4.21 |
| ± | MeO— | 5-F— | 1 | —Me | 1636 | 88 | $C_{17}H_{22}FNO_2$ | 70.08 69.92 | 7.61 7.66 | 4.81 4.63 |
| ± | MeO— | 5-F— | 1 | -n-Pr | 1642 | 77 | $C_{19}H_{26}FNO_2$. 0.25 $H_2O$ | 70.45 70.38 | 8.25 8.19 | 4.32 4.14 |
| ± | MeO— | H— | 1 | -2-Thienyl | 1614 | 74 | $C_{20}H_{23}NO_2S$ | 70.35 70.09 | 6.79 7.07 | 4.1 4.05 |
| ± | 3-OMe—Ph—(CH₂)₃—O— | H | 1 | -c-Pr | 1635 | 70 | $C_{28}H_{35}NO_3$. 0.3 $CH_2Cl_2$ | 74.24 73.84 | 7.76 8.05 | 3.03 3.07 |
| ± | H— | H | 1 | -c-Pr | 1636 | 90 | $C_{18}H_{23}NO$. 0.1 $CH_2Cl_2$ | 78.32 78.12 | 8.38 8.49 | 5.02 4.88 |

Example 10

Alternate Method for the Preparation of Amides 1-[(3-Furanyl)carbonyl]4-(6-methoxy-indan-1-yl)-piperidine A solution of 4-(6-methoxy-indan-1-yl)piperidine (110 mg, 0.48 mmol) in $CH_2Cl_2$ (2 l) was added to a mixture of furan-3-carboxylic acid (69.5 mg, 0.62 mmol) and 1-(3-dimethylaminopropyl)-3-ethylcarbodiimide methiodide (EDCI, 125 mg, 0.65 mmol) in $CH_2Cl_2$ (3 ml) and shaken for 4 days. The reaction mixture was filtered through a mixture of SCX Bondesil® (Varian #1221-3039, 2 g) and SAX Bondesil® (Varian #1221-3042, 2 g), and washed off the column with $CH_2Cl_2$ (15 ml). The $CH_2Cl_2$ solution was concentrated in vacuo to give the product as an viscous oil (67 mg, 43%). IR (KBr) 2936, 2852, 1620, 1570, 1504, 1490, 1442 $cm^{-1}$; ES-MS: 326.2 ($MH^+$). Anal Calc'd for $C_{20}H_{23}NO_3 \cdot 0.2\ H_2O$: C, 73.01%; H, 7.17%; N, 4/26%. Found: C, 73.01%; H, 7.94%; N, 4.44%.

Table 3 lists additional compounds of Formula I that were prepared by this method.

Example 11

N-Cyclopropylcarbonyl-4-(6-hydroxy-indan-1-yl)piperidine

A 1M boron tribromide solution (3 mL, 3 mmol) was added at −78 °C. to a solution of N-cyclopropylcarbonyl-4-(6-methoxy-indan-1-yl)piperidine (0.45 g, 1.5 mmol) in methylene chloride. After stirring for 18 h the reaction was quenched with water. The organic layer was separated and washed with 1N NaOH solution and concentrated in vacuo. The residue was stirred for 18 h with a mixture of methanol and 1N NaOH. The methanol was removed in vacuo and the solution was made acid with 1N HCl. The insolubles were collected by filtration to give 0.15 g product, mp 75°–82° C. Anal. Calc'd for $C_{18}H_{23}NO_2 \cdot 0.3\ H_2O$: C, 74.35%; H, 8.18%; N, 4.82%. Found: C, 74.4%; H, 8.08%; N, 4.74%.

Example 12

Measurement of Binding to Human Melatonergic Receptors

The melatonergic binding affinities of various compounds of Formula I were determined by the method of Reppert, S.

TABLE 3

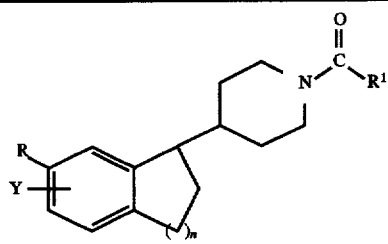

| +/− | R | Y | m | R¹ | IR νCO $cm^{-1}$ | % | empirical formula | Calcd %C | %H | %N | Found %C | %H | %N |
|---|---|---|---|---|---|---|---|---|---|---|---|---|---|
| ± | MeO— | H— | 1 | 3-methyl-2-thienyl | 1624 | 64 | $C_{21}H_{25}NO_2S \cdot 0.2\ H_2O$ | 70.24 | 7.13 | 3.90 | 70.37 | 7.47 | 3.90 |
| ± | MeO— | H— | 1 | 1,2,3-Thiadiazol-4-yl | 1630 | 26 | $C_{18}H_{21}N_3O_2S$ | 62.95 | 6.16 | 12.23 | 62.96 | 6.50 | 11.83 |
| ± | MeO— | H— | 1 | 1-Methyl-2-pyrrolyl | 1618 | 36 | $C_{21}H_{26}N_2O_2 \cdot 0.15\ H_2O$ | 73.93 | 7.77 | 8.21 | 73.94 | 8.11 | 8.19 |
| ± | MeO— | H— | 1 | 2-Chloro-3-OMe-2-thienyl | 1634 | 65 | $C_{21}H_{24}NO_3SCl \cdot 0.2\ CH_2Cl_2$ | 60.43 | 5.78 | 3.29 | 60.45 | 6.10 | 3.22 |
| ± | MeO— | H— | 1 | 2-pyrrolyl | 1588 | 33 | $C_{20}H_{24}N_2O_2 \cdot 0.15\ H_2O$ | 73.43 | 7.49 | 8.56 | 73.46 | 7.53 | 8.43 |
| ± | MeO— | H— | 1 | 3-Chloro-2-thienyl | 1630 | 64 | $C_{20}H_{22}NO_2SCl$ | 63.90 | 5.90 | 3.73 | 63.75 | 6.06 | 3.70 |
| ± | MeO— | H— | 1 | 3-Me-2-furanyl | 1620 | 32 | $C_{21}H_{25}NO_3$ | 74.31 | 7.42 | 4.13 | 74.16 | 7.53 | 3.88 |
| ± | MeO— | H— | 1 | 3-Thienyl | 1624 | 42 | $C_{20}H_{23}NO_2S \cdot 0.25\ CH_2Cl_2 \cdot 0.05\ H_2O$ | 68.81 | 6.78 | 3.99 | 68.73 | 7.02 | 3.86 |
| ± | MeO— | H— | 1 | 5-Methyl-2-thienyl | 1612 | 53 | $C_{21}H_{25}NO_2S \cdot 0.3\ H_2O$ | 69.89 | 7.15 | 3.88 | 69.89 | 7.24 | 3.81 |
| ± | MeO— | H— | 1 | -2-Furanyl | 1622 | 38 | $C_{20}H_{23}NO_3 \cdot 0.5\ CH_2Cl_2$ | 67.46 | 6.47 | 3.75 | 67.76 | 6.81 | 3.82 |
| ± | MeO— | H— | 1 | —$CH_2$—SMe | 1638 | 35 | $C_{18}H_{25}NO_2S \cdot 0.15\ H_2O$ | 67.11 | 7.92 | 4.35 | 67.09 | 8.20 | 4.34 |
| ± | MeO— | H— | 1 | —CHMeEt | 1640 | 51 | $C_{20}H_{29}NO_2 \cdot 0.2\ H_2O$ | 75.29 | 9.29 | 4.39 | 75.36 | 9.72 | 4.03 |
| ± | MeO— | H— | 1 | —$CMe_2Et$ | 1626 | 38 | $C_{21}H_{31}NO_2 \cdot 0.25\ H_2O$ | 75.52 | 9.51 | 4.19 | 75.49 | 9.69 | 4.17 |
| ± | MeO— | H— | 1 | -c-Penten-1-yl | 1608 | 53 | $C_{21}H_{27}NO_2 \cdot 0.2\ H_2O \cdot 0.1\ CH_2Cl_2$ | 75.17 | 8.21 | 4.14 | 75.09 | 8.52 | 4.15 |

M., Weaver, D. R., and Ebisawa, R. (*Neuron*, Volume 13, 1177–1185, 1994). The assays were incubated at 37° C. for 1 hour, and the reaction was terminated by filtration. The filters were washed with wash buffer. Compounds with $IC_{50}$ affinity values at or below 250 nM are termed active. The reagents, membrane and other techniques used in the melatonergic binding assays are more fully described below:

1. Reagents:
   (a) 50 mM Tris buffer containing 12.5 mM $MgCl_2$, and 2 mM EDTA, pH 7.4 at 37° C.
   (b) Wash buffer: 20 mM Tris base containing 2 mM $MgCl_2$, pH 7.4 at room temperature.
   (c) Melatonin ($10^{-5}$M final concentration).
   (d) 2-[$^{125}$I]-Iodomelatonin, 200 pM final concentration Source: NEN 2. Membrane preparation: NIH 3T3 cells stably transfected with the human $ML_{1B}$ receptor were obtained from S. M. Reppert and maintained. Cells were pelleted when confluent. The supernatant was discarded and the pellets frozen. For preparing membrane homogenates, the pellets are thawed on ice and resuspended in TME buffer, Tris base, $MgCl_2$, EDTA (pH 7.4 at 37° C.), supplemented with aprotinin, leupeptin, and phenylmethlysulfonylfluoride. The cells were then homogenized and centrifuged. The resulting pellet was resuspended with a Dounce homogenizer in TME and frozen. At assay, a small aliquot was thawed on ice and resuspended in TME buffer.

The compounds of Formula I having $IC_{50}$ values for melatonin binding of 250 nM or less are considered active and are listed in Table 4, along with luzindole.

TABLE 4

Binding of Selected Compounds to Melatonergic Receptors.

| Melatonin Binding | Compound |
| --- | --- |
| *** | N-Ethyl-4-[6-(n-heptyloxy)-indan-1-yl]piperidine-1-carboxamide |
| ** | N-Ethyl-4-[6-[3-(3-methoxyphenyl)propyloxy]-indan-1-yl]piperidine-1-carboxamide |
| ** | 1-(Cyclopropylcarbonyl)-4-[6-[3-(methoxyphenyl)propyloxy]indan-1-yl]piperidine |
| ** | N-Ethyl-4-(indan-1-yl)-piperidine-1-carboxamide |
| *** | N-Methyl-4-(indan-1-yl)-piperidine-1-carboxamide |
| *** | 1-(Cyclopropylcarbonyl)-4-(indan-1-yl)piperidine |
| *** | N-Methyl-4-(6-methoxy-indan-1-yl)-piperdine-1-thiocarboxamide |
| *** | N-Cyclproylcarbonyl-4-(6-methoxy-indan-1-yl)piperidine |
| *** | 4-(6-methoxy-indan-1-yl)-1-(2-methylpropanoyl)piperidine |
| *** | 4-(6-Methoxy-indan-1-yl)-1-(2-methylbutanoyl)piperidine |
| *** | 4-(6-Methoxy-indan-1-yl)-1-(2-methylthioacetyl)piperidine |
| *** | 1-[(Cyclopent-1-en-1-yl)carbonyl[-4-(6-methoxy-indan-1-yl)piperidine |
| *** | (−)-4-(6-methoxy-indan-1-yl)-1-(trifluoroacetyl)piperidine |
| *** | 4-(6-methoxy-indan-1-yl)-1-(trifluoroacetyl)piperidine |
| *** | (−)-1-Formyl-4-(6-methoxy-indan-1-yl)piperidine |
| *** | 1-Formyl-4-(6-methoxy-indan-1-yl)piperidine |
| *** | (−)-1-(Cyclopropylcarbonyl)-4-(6-methoxy-indan-1-yl)piperidine |
| *** | (+)-1-(Cyclopropylcarbonyl)-4-(6-methoxy-indan-1-yl)piperidine |
| *** | 4-(6-Methoxy-indan-1-yl)-1-(2-methoxy-acetyl)piperidine |
| *** | (−)-4-(6-Methoxy-indan-1-yl)-1-(2-methoxyacetyl)piperidine |
| *** | (−)-4-(6-Methoxy-indan-1-yl)-1-(2-methyl-propanoyl)piperidine |
| *** | 1-(Cyclopropylcarbonyl)-4-(5-fluoro-6-methoxy-indan-1-yl)piperidine |
| *** | 4-(5-Fluoro-6-methoxy-indan-1-yl)1-(2-methylpropanoyl)piperidine |
| *** | (−)-4-(6-Methoxy-indan-1-yl)-1-pentanoylpiperidine |
| *** | (−)-1-Butanoyl-4-(6-methoxy-indan-1-yl)piperidine |
| *** | (−)-4-(6-Methoxy-indan-1-yl)-1-propanoylpiperidine |
| *** | (−)-1-Acetyl-4-(6-methoxy-indan-1-yl)piperidine |
| *** | 1-Butanoyl-4-(5-fluoro-6-methoxy-indan-1-yl)piperidine |
| *** | 4-(5-Fluoro-6-methoxy-indan-1-yl)-1-propanoylpiperidine |

TABLE 4-continued

Binding of Selected Compounds to Melatonergic Receptors.

| Melatonin Binding | Compound |
| --- | --- |
| *** | 1-Acetyl-4-(5-fluoro-6-methoxy-indan-1-yl)piperidine |
| *** | 1-(Cyclopropylcarbonyl)-4-(6-fluoro-indan-1-yl)piperidine |
| *** | 4-(6-Fluoro-indan-1-yl)-1-(2-methylpropanoyl)piperidine |
| *** | 1-Butanoyl-4-(6-fluoro-indan-1-yl)piperidine |
| *** | 4-(6-Ethyl-indan-1-yl)-1-(2-methylpropanoyl)piperidine |
| *** | 1-(Cyclopropylcarbonyl)-4-(6-ethyl-indan-1-yl)piperidine |
| ** | 1-(2,2-Dimethyl-butanoyl)-4-(6-methoxy-indan-1-yl)piperidine |
| ** | (+)-4-(6-Methoxy-indan-1-yl)-1-(trifluoroacetyl)piperidine |
| ** | (+)-1-Formyl-4-(6-methoxy-indan-1-yl)piperidine |
| ** | (+)-4-(6-Methoxy-indan-1-yl)-1-(2-methylpropanoyl)piperidine |
| ** | N-(Cyclopropylcarbonyl-4-(6-hydroxy-indan-1-yl)-piperidine |
| ** | 1-(Cyclopropylcarbonyl)-4-[6-(trifluoromethoxy)-indan-1-yl]piperidine |
| * | (+)-1-(2-Methoxyacetyl)-4-(6-methoxy-indan-1-yl)piperidine |
| *** | 4-(6-Methoxy-indan-1-yl)-1-[(2-thienyl)carbonyl]piperidine |
| *** | 1-[(2-Furanyl)carbonyl]-4-(6-methoxy-indan-1-yl)-piperidine |
| *** | 4-(6-Methoxy-indan-1-yl)-1-[(1H-pyrrol-2-yl)-carbonyl]piperidine |
| *** | 4-(6-Methoxy-indan-1-yl)-i- [(3-methyl-furan-2-yl)carbonyl]piperidine |
| *** | 1-[(3-Furanyl)carbonyl]4-(6-methoxy-indan-1-yl)-piperidine |
| *** | 4-(6-Methoxy-indan-1-yl)-1-[(1-methyl-pyrrol-2-yl)carbonyl]piperidine |
| *** | 4-(6-Methoxy-indan-1-yl)-1-[(3-methyl-thien-2-yl)carbonyl]piperidine |
| *** | 4-(6-Methoxy-indan-1-yl)-1-[(3-thienyl)carbonyl]piperidine |
| *** | 1-[(3-Chloro-thien-2-yl)carbonyl]-4-(6-methoxy-indan-1-yl)-piperidine |
| *** | 4-(6-Methoxy-indan-1-yl)-1-[(1,2,3-thiadiazol-4-yl)carbonyl]piperidine |
| ** | 4-(6-methoxy-indan-1-yl)-1-[(5-methyl-thien-2-yl)carbonyl]piperidine |
| ** | 1-[(2-Chloro-3-methoxythien-4-yl)carbonyl]4-(6-methoxy-indan-1-yl)piperidine |
| *** | N-Ethyl-4-(6-methoxy-indan-1-yl)piperidine-1-carboxamide |
| *** | N-Methyl-4-(6-methoxy-indan-1-yl)piperidine-1-carboxamide |
| *** | (−)-N-Ethyl-4-(6-methoxy-indan-1-yl)piperidine-1-carboxamide |
| *** | (−)-N-Methyl-4-(6-methoxy-indan-1-yl)piperidine-1-carboxamide |
| *** | (−)-N,N-Dimethyl-4-(6-methoxy-indan-1-yl)piperidine-1-carboxamide |
| *** | N-Methyl-4-(5-fluoro-6-methoxy-indan-1-yl)piperidine-1-carboxamide |
| *** | N-Ethyl-4-(6-fluoro-indan-1-yl)piperidine-1-carboxamide |
| *** | N-Ethyl-4-(6-ethyl-indan-1-yl)piperidine-1-carboxamide |
| ** | (+)N-Ethyl-4-(6-methoxy-indan-1-yl)piperidine-1-carboxamide |
| ** | (+)-N-Methyl-4-(6-methoxy-indan-1-yl)piperidine-1-carboxamide |
| ** | N-Ethyl-4-(5-fluoro-6-methoxy-indan-1-yl)piperidine-1-carboxamide |
| ** | N-Methyl-4-(6-fluoro-indan-1-yl)piperidine-1-carboxamide |
| ** | N-Ethyl-4-[6-(trifluoromethoxy)-indan-1-yl]piperidine-1-carboxamide |
| *** | 1-(Cyclopropylcarbonyl)-4-(7-methoxy-tetralin-1-yl)piperidine |
| ** | N-Ethyl-4-(7-methoxy-tetralin-1-yl)piperidine-1-carboxamide |
| * | Luzindole |

*: 250 nM > $IC_{50}$ > 100 nM;
**: 100 nM > $IC_{50}$ > 10 nM;
***: $IC_{50}$ < 10 nM.

Reasonable variations, such as those which would occur to a skilled artisan, can be made herein without departing from the scope of the invention.

We claim:

1. A compound of Formula I:

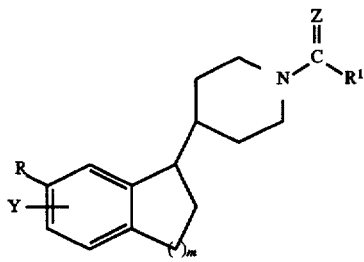

wherein:

R is H, $C_{1-7}$ alkoxy, halogen, hydroxyl, $C_{1-4}$ haloalkoxy or $C_{1-4}$ alkoxyphenyl $C_{1-7}$ alkoxy;

Y is hydrogen or halogen;

Z is O or S;

m is 1 or 2; and $R^1$ is hydrogen, $C_{1-6}$ straight or branched alkyl, $C_{1-6}$ straight or branched haloalkyl, $C_{2-8}$ alkylthioalkyl, $C_{2-8}$ alkyloxyalkyl, $C_{2-6}$ straight or branched alkenyl, $C_{3-5}$ cycloalkyl, $C_{3-5}$ cycloalkenyl, thienyl, furanyl, thiadiazolyl, pyrrolyl, $C_{1-6}$ alkylthio or $NR^2R^3$, in which $R^2$ and $R^3$ are independently hydrogen or $C_{1-4}$ alkyl.

2. The compound of claim 1 wherein R is methoxy.

3. The compound of claim 2 wherein m is 1 and $R^1$ is $C_{3-5}$ cycloalkyl, thienyl or furanyl.

4. The compound of claim 3 selected from the group consisting of:

1-(Cyclopropylcarbonyl)-4-(6-methoxy-indan-1-yl)piperidine;

4-(6-Methoxy-indan-1-yl)-1-[(2-thienyl)carbonyl]piperidine;

(−)-1-(Cyclopropylcarbonyl)-4-(6-methoxy-indan-1-yl)piperidine;

(+)-1-(Cyclopropylcarbonyl)-4-(6-methoxy-indan-1-yl)piperidine;

1-(Cyclopropylcarbonyl)-4-(5-fluoro-6-methoxy-indan-1-yl)piperidine; and 1-(Cyclopropylcarbonyl)-4-(6-hydroxy-indan-1-yl)piperidine.

5. The compound of claim 2 wherein $R^1$ is $NR^2R^3$.

6. The compound of claim 5 selected from the group consisting of:

N-Ethyl-4-(6-methoxy-indan-1-yl)piperidine-1-carboxamide;

N-Methyl-4-(6-methoxy-indan-1-yl)piperidine-1-carboxamide;

(−)-N-Ethyl-4-(6-methoxy-indan-1-yl)piperidine-1-carboxamide;

(−)-N-Methyl-4-(6-methoxy-indan-1-yl)piperidine-1-carboxamide;

N-Ethyl-4-(5-fluoro-6-methoxy-indan-1-yl)piperidine-1-carboxamide;

(−)-N,N-Dimethyl-4-(6-methoxy-indan-1-yl)piperidine-1-carboxamide;

N-Methyl-4-(5-fluoro-6-methoxy-indan-1-yl)piperidine-1-carboxamide;

N-Ethyl-4-(7-methoxy-tetralin-1-yl)piperidine-1-carboxamide; and

N-Ethyl-4-(6-fluoro-indan-1-yl)piperidine-1-carboxamide.

7. The compound of claim 2 wherein $R^1$ is $C_{1-4}$ alkyl or $C_{1-4}$ haloalkyl.

8. The compound of claim 7 selected from the group consisting of:

4-(6-Methoxy-indan-1-yl)-1-(2-methylpropanoyl)piperidine;

(−)-4-(6-Methoxy-indan-1-yl)-1-(trifluoroacetyl)piperidine;

4-(6-Methoxy-indan-1-yl)-1-(trifluoroacetyl)piperidine;

(−)-4-(6-Methoxy-indan-1-yl)-1-(2-methylpropanoyl)piperidine;

4-(5-Fluoro-6-methoxy-indan-1-yl)1-(2-methylpropanoyl)piperidine;

(−)-4-(6-Methoxy-indan-1-yl)-1-pentanoylpiperidine;

(−)-1-Butanoyl-4-(6-methoxy-indan-1-yl)piperidine;

(−)-4-(6-Methoxy-indan-1-yl)-1-propanoylpiperidine;

(−)-1-Acetyl-4-(6-methoxy-indan-1-yl)piperidine;

1-Butanoyl-4-(5-fluoro-6-methoxy-indan-1-yl)piperidine;

4-(5-Fluoro-6-methoxy-indan-1-yl)-1-propanoylpiperidine; and

1-Acetyl-4-(5-fluoro-6-methoxy-indan-1-yl)piperidine.

9. The compound of claim 2 wherein $R^1$ hydrogen.

10. The compound of claim 9 selected from the group consisting of:

(−)-1-Formyl-4-(6-methoxy-indan-1-yl)piperidine; and

1-Formyl-4-(6-methoxy-indan-1-yl)piperidine.

11. The compound of claim 2 wherein m=2.

12. The compound of claim 11 selected from the group consisting of:

N-Ethyl-4-(7-methoxy-tetralin-1-yl)piperidine-1-carboxamide; and 1-(Cyclopropylcarbonyl)-4-(7-methoxy-tetralin-1-yl)piperidine.

13. The compound of claim 2 selected from the group consisting of:

1-[(2-Furanyl)carbonyl]-4-(6-methoxy-indan-1-yl)-piperidine;

4-(6-Methoxy-indan-1-yl)-1-[(1H-pyrrol-2-yl)carbonyl]piperidine;

4-(6-Methoxy-indan-1-yl)-1-[(3-methyl-furan-2-yl)carbonyl]piperidine;

1-[(3-Furanyl)carbonyl]4-(6-methoxy-indan-1-yl)-piperidine;

4-(6-Methoxy-indan-1-yl)-1-[(1-methyl-pyrrol-2-yl)carbonyl]piperidine;

4-(6-Methoxy-indan-1-yl)-1-[(3-methyl-thien-2-yl)carbonyl]piperidine;

4-(6-Methoxy-indan-1-yl)-1-[(3-thienyl)carbonyl]piperidine;

1-[(3-Chloro-thien-2-yl)carbonyl]-4-(6-methoxy-indan-1-yl)piperidine;

4-(6-Methoxy-indan-1-yl)-1-[(1,2,3-thiadiazol-4-yl)carbonyl]piperidine;

4-(6-Methoxy-indan-1-yl)-1-(2-methylbutanoyl)piperidine;

4-(6-Methoxy-indan-1-yl)-1-(2-methylthioacetyl)piperidine;

1-[(Cyclopent-1-en-1-yl)carbonyl]-4-(6-methoxy-indan-1-yl)piperidine;

(−)-4-(6-Methoxy-indan-1-yl)-1-(2-methoxyacetyl)piperidine; and

N-Methyl-4-(6-methoxy-indan-1-yl)-piperidine-1-thiocarboxamide.

14. The compound of claim 1 selected from the group consisting of:

1-(Cyclopropylcarbonyl)-4-(6-fluoro-indan-1-yl)piperidine;

4-(6-Fluoro-indan-1-yl)-1-(2-methylpropanoyl)piperidine;

1-Butanoyl-4-(6-fluoro-indan-1-yl)piperidine;

4-(6-Ethyl-indan-1-yl)-1-(2-methylpropanoyl)piperidine;

1-(Cyclopropylcarbonyl)4-(6-ethyl-indan-1-yl)piperidine;

N-Ethyl-4-(6-fluoro-indan-1-yl)piperidine-1-carboxamide;

N-Ethyl-4-(6-ethyl-indan-1-yl)piperidine-1-carboxamide;

N-Ethyl-4-[6-(n-heptyloxy)-indan-1-yl]piperidine-1-carboxamide;

1-(Cyclopropylcarbonyl)-4-(indan-1-yl)piperidine; and

N-Methyl-4-(indan-1-yl)-piperidine-1-carboxamide.

15. The compound of claim 1, (−)-1-(Cyclopropylcarbonyl)-4-(6-methoxy-indan-1-yl)piperidine.

16. The compound of claim 1, (−)-4-(6-Methoxy-indan-1-yl)-1-(2-methylpropanoyl)piperidine.

17. The compound of claim 1, 1-(Cyclopropylcarbonyl)-4-(5-fluoro-6-methoxy-indan-1-yl)piperidine.

18. The compound of claim 1, (−)-N-Methyl-4-(6-methoxy-indan-1-yl)piperidine-1-carboxamide.

19. The compound of claim 2 wherein m is 1 and $R^1$ is methylfuranyl, methylthienyl, halothienyl, thiadiazolyl or pyrrolyl.

20. The compound of claim 19 selected from:

4-(6-Methoxy-indan-1-yl)-1-[(1H-pyrrol-2-yl)carbonyl]piperidine;

4-(6-Methoxy-indan-1-yl)-1-[(3-methyl-furan-2-yl)carbonyl]piperidine;

4-(6-Methoxy-indan-1-yl)-1-[(3-methyl-thien-2-yl)carbonyl]piperidine;

1-[(3-Chloro-thien-2-yl)carbonyl]-4-(6-methoxy-indan-1-yl)piperidine; and 4-(6-Methoxy-indan-1-yl)-1-[(1,2,3-thiadiazol-4-yl)carbonyl]piperidine.

21. A pharmaceutical composition for treating a sleep or circadian rhythm disorder in a patient in need of such treatment comprising an effective amount of a compound of claim 1 and a suitable amount of a pharmaceutically acceptable carrier.

22. A method of treating a sleep disorder in a patient in need of such treatment comprising the administration to said patent of an effective amount of a compound of claim 1.

23. A pharmaceutical composition for treating depression in a patient in need of such treatment comprising an effective amount of a compound of claim 1 and a suitable amount of a pharmaceutically acceptable carrier.

24. A method of treating depression in a patient in need of such treatment comprising the administration to said patient of an effective amount of a compound of claim 1.

* * * * *